United States Patent [19]

Sasse et al.

[11] Patent Number: 4,698,344

[45] Date of Patent: Oct. 6, 1987

[54] 1-HETEROARYL-4-ARYL-PYRAZOLIN-5-ONES FOR USE AS MEDICAMENTS

[75] Inventors: Klaus Sasse, Bergisch Gladbach, Fed. Rep. of Germany; Michael Hammond, Postcombe, United Kingdom; Friedel Seuter, Wuppertal, Fed. Rep. of Germany; Elisabeth Perzborn, Wuppertal, Fed. Rep. of Germany; Bernhard Pelster, Augustin, Fed. Rep. of Germany; Graham Sturton, Slough; Trevor Abram, Marlow, both of United Kingdom

[73] Assignee: Bayer Aktiengesellschaft, Leverkusen, Fed. Rep. of Germany

[21] Appl. No.: 800,485

[22] Filed: Nov. 21, 1985

[30] Foreign Application Priority Data

Nov. 28, 1984 [DE]  Fed. Rep. of Germany ....... 3443308

[51] Int. Cl.$^4$ .................. A61K 31/505; A61K 31/44

[52] U.S. Cl. .................. 514/275; 514/341; 514/404

[58] Field of Search .............. 514/275, 341, 404; 544/331

[56]  References Cited

U.S. PATENT DOCUMENTS 4,032,646  6/1977  Möller et al. ............. 514/404

OTHER PUBLICATIONS

Chem. Abstr., 49699w, Matsuura et al., "1-(4-Halo-6-lower alkyl-2-pyrimidinyl . . . ", v. 81, No. 9, (Sep. 1974), p. 395.

Primary Examiner—Leonard Schenkman
Attorney, Agent, or Firm—Sprung Horn Kramer & Woods

[57]  ABSTRACT

The invention relates to 1-heteroaryl-4-aryl-pyrazolin-5-ones, a preparation process and the use in combating diseases, in particular for use as lipoxygenase inhibitors.

4 Claims, No Drawings

1-HETEROARYL-4-ARYL-PYRAZOLIN-5-ONES FOR USE AS MEDICAMENTS

The present invention relates to 1-heteroaryl-4-aryl-pyrazolin-5-ones as medicaments.

The invention also relates to the use of pyrazolinones as inhibitor/stimulators of enzymatic reactions in the context of arachidonic acid metabolism. Such substances are suitable for the prevention and treatment of diseases of the respiratory tract, such as allergies/asthma, bronchitis, emphysema, shock lung, pulmonary hypertension, inflammations/rheumatism, arthroses and oedemas, thromboses and thromboembolisms, ischaemias (disorders in peripheral, cardiac and cerebral circulation), cardiac and cerebral infarction, disorders in cardiac rhythm, angina pectoris and arteriosclerosis, for tissue transplantations, dermatoses such as psoriasis, and for cytoprotection in the gastrointestinal tract.

The invention also relates to medicaments which are characterized in that they contain a therapeutically effective amount of pyrazolinones.

The compounds according to the invention are preferential inhibitors of lipoxygenase and at the same time stimulate prostacyclin synthesis. Known lipoxygenase inhibitors, such as nordihydroguaretic acid, 3-amino-1-(3-trifluoromethylphenyl)-pyrazoline (BW 755C), phenidone and 5,8,11,14-eicosatetraynoic acid are either simultaneously active as cyclooxygenase inhibitors or active only at very high concentrations. Inhibition of the enzyme cyclooxygenase in the arachidonic acid metabolism leads to a global inhibition of prostaglandin synthesis and in general to stimulation of the lipoxygenase route, which can cause gastrotoxicity and pro-inflammatory and asthmatic actions, as well as an increased tendency towards thrombosis and arteriosclerosis.

Known Lipoxygenase inhibitors, such as 3-amino-1-(m-trifluoromethylphenyl)-2-pyrazoline, furthermore have toxic side effects when administered systemically (for example orally). There is therefore a need for compounds which have a more potent action and a more selective action profile without side effects.

Surprisingly, the pyrazolinones according to the invention comply with the required pharmacological profile.

Since the discovery of the "slow reacting substance of anaphylaxis (SRS-A)", it has been attributed an important role in cases of asthmatic bronchoconstriction and inflammation. It is formed via the lipoxygenase route of arachidonic acid metabolism and is identified as leukotriene (s) (LTD$_4$, LTC$_4$, LTE$_4$). Corresponding inhibitors are therefore potential antiasthmatics. However, the compounds which have so far been disclosed do not meet the requirements or cannot be used therapeutically.

Pyrazolinones for use as medicaments in accordance with the present invention are of the formula

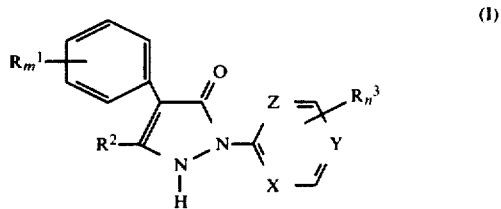

(I)

in which

R$^1$ is hydrogen, halogen, hydroxyl, optionally substituted lower alkoxy, optionally substituted phenoxy, optionally substituted lower alkylmercapto, optionally substituted lower alkylsulphonyl, optionally fluorine-substituted lower alkyl, a fused-on carbocyclic or heterocyclic radical, carboxyl, lower alkoxycarbonyl or one of the groups

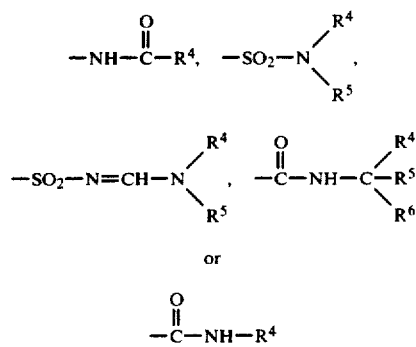

or

wherein

R$^4$, R$^5$ and R$^6$ are identical or different and denote hydrogen, lower alkyl or phenyl, m denotes an integer from 1 to 5, R$^2$ denotes hydrogen or lower alkyl, X, Y and Z denotes an N atom or a ring member $$\overset{R^3}{\underset{}{=C-}},$$

at least one of the radicals X, Y or Z denoting an N atom,

R$^3$ denotes hydrogen, halogen, lower alkoxy, lower alkylmercapto, lower alkyl, lower halogenoalkyl, nitro, cyano, carboxylic acid amide or a fused-on phenylene radical and n denotes an integer from 1 to 4.

The pyrazolinones according to the invention can exist in tautomeric forms:

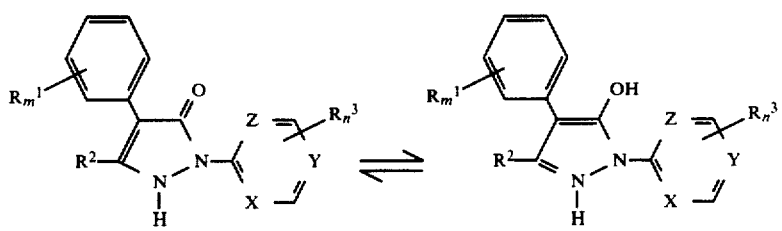

In the context of the present invention, the substituents can in general have the following meaning: halogen in general denotes fluorine, chlorine, bromine or iodine, preferably fluorine and chlorine.

Lower alkyl in general denotes a straight-chain or branched hydrocarbon radical with 1 to about 6 carbon atoms. The following lower alkyl radicals may be mentioned as examples: methyl, ethyl, propyl, isopropyl, butyl, isobutyl, pentyl, isopentyl, hexyl and isohexyl. The methyl and ethyl radicals are preferred.

Lower alkoxy in general denotes a straight-chain or branched hydrocarbon radical which has 1 to about 6 carbon atoms and is bonded via oxygen. The following lower alkoxy radicals may be mentioned as examples: methoxy, ethoxy, propoxy, isopropoxy, butoxy, isobutoxy, pentoxy, isopentoxy, hexoxy and isohexoxy. The methoxy and ethoxy radicals are preferred.

In the lower alkylmercapto, lower alkylsulphonyl and lower alkyl ester radicals, the lower alkyl radical in general has the abovementioned scope of meaning.

The following radicals may be mentioned as examples of possible substituents: methylmercapto, isopropylmercapto, trifluoromethylmercapto, methylsulphonyl, ethylsulphonyl, butylsulphonyl, methoxycarbonyl, ethoxycarbonyl and tert.-butoxycarbonyl.

The radical $R^1$ can represent a carbocyclic or heterocyclic radical which is fused on to the phenyl nucleus. In general, it is a 5-membered or 6-membered ring which, in addition to hydrocarbon members, can also contain one or two heteroatoms, preferably nitrogen, oxygen or sulphur. The following carbocyclic or heterocyclic rings may be mentioned as examples: benzene, furan, thiophene, pyrrole, dioxolene, dioxene, pyridine, pyrimidine, pyrazine, pyridazine, imidazole, triazole, oxazole, thiazole, thiadiazole and the like.

Preferred pyrazolinones are those of the formula

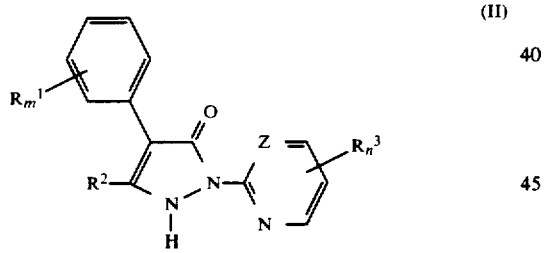

(II)

in which
$R^1$ denotes hydrogen, fluorine, chlorine, methyl, ethyl, methoxy, ethoxy, trifluoromethyl, trifluoromethoxy or trifluoromethylmercapto,
m represents the number 1 or 2,
$R^2$ denotes hydrogen, methyl or ethyl,
$R^3$ denotes hydrogen, fluorine, chlorine, methyl, ethyl, methoxy or ethoxy and
n represents the number 1 or 2.

The following preferred pyrazolinones may be mentioned specifically:

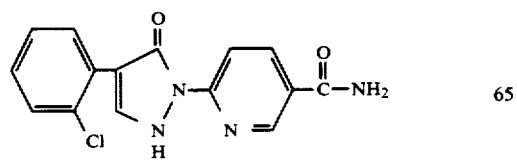

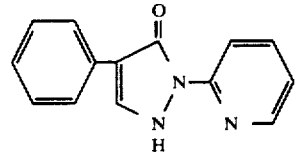

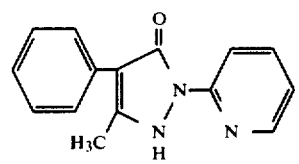

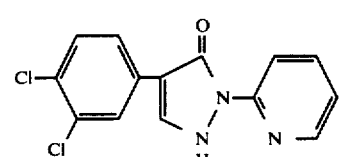

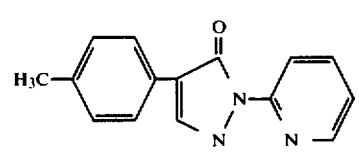

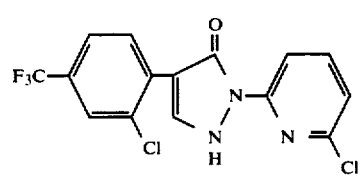

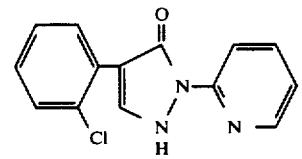

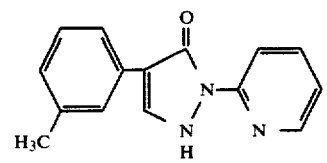

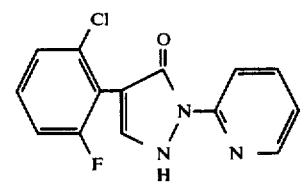

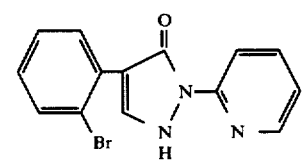

-continued
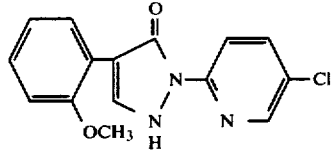
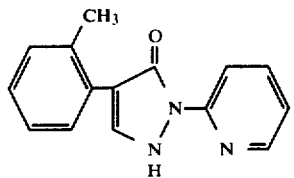
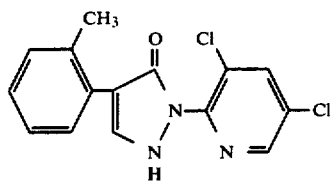
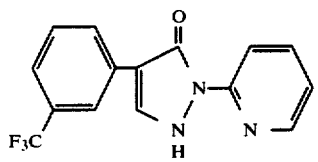
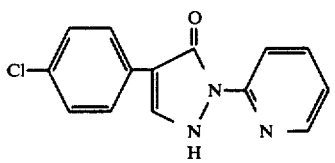
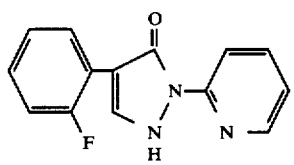
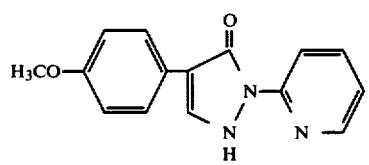
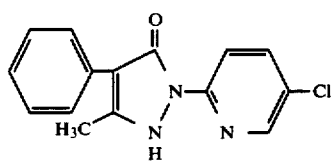
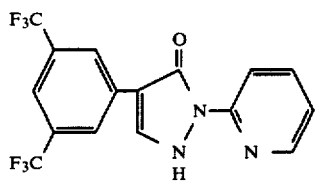
-continued
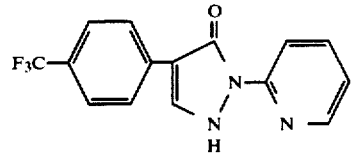
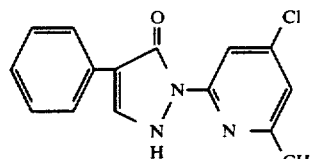
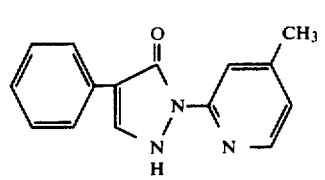
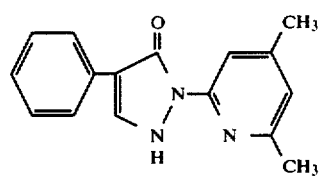
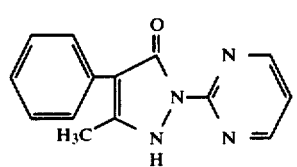
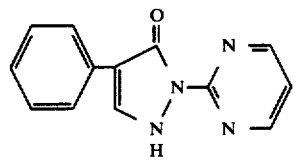
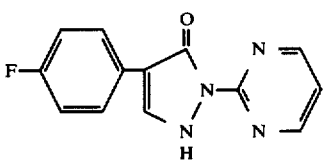
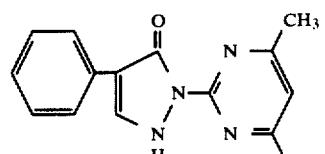
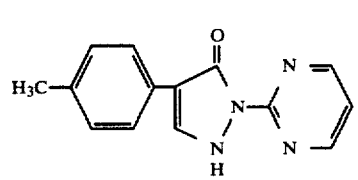

In formula III and IV, $R^1$, $R^2$, $R^3$, X, Y, Z, n and m have the same meaning as in formula I. R' represents an OH group, a lower alkoxy group, halogen, an R'''—$SO_2$—O— group or a dialkylamino group and R'' represents a lower alkyl radical or an aryl radical.

The precursors of the formula III required for the preparation of the compounds of the formula I according to the invention are known in principle. In the case where R represents a hydrogen atom, these are obtained from correspondingly substituted phenylacetic acid alkyl esters by reaction with a formic acid derivative. Thus, compounds III where R'=OH are prepared by the action of methyl or ethyl formate in the presence of strong bases, such as alkali metal alcoholates, sodium amide or the like (B. 20, 2931 (1887); B. 28, 771 (1895); Ann. 291, 164 (1896), whereupon the alkali metal salts (III; R'=0-Met.) are initially formed and can also be used directly in the subsequent reaction or are converted into the free hydroxymethylene compounds by treatment with aqueous acids, these compounds being in tautomeric equilibrium with the corresponding α-formyl-L-phenylacetic esters.

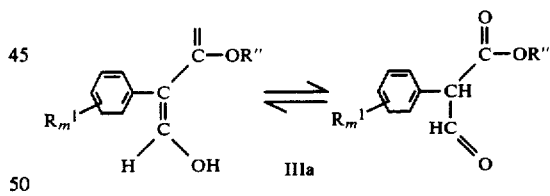

According to the literature, compounds where R'=OAlk are prepared by the action of alkylating agents on compounds III where R'=OH under basic conditions (Ann. 424, 228 (1921); J. Chem. Soc. 1953, 3548; and J. org. Chem. 45, 2576 (1980)) or by etherification of the same compounds with alcohols in the presence of p-toluene-sulphonic acid (J. chem. Soc. 1953, 3548).

The compounds of the formula I according to the invention can be prepared by a process in which α-acylphenylacetic acid esters or derivatives thereof of the formula III are reacted with hydrazino-heterocyclic compounds of the formula IV.

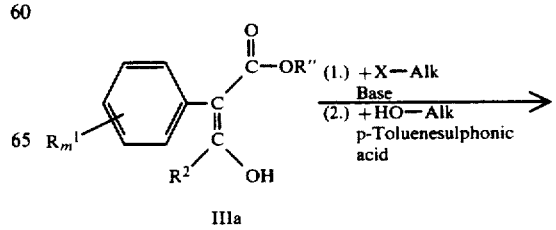

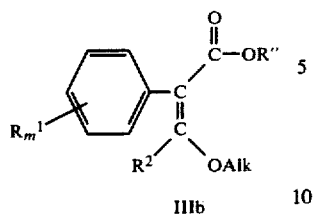

IIIb

Compounds III where R′=R‴—SO$_2$—O— group can be prepared from the corresponding compounds III where R′=OH by reaction with sulphonic acid chlorides, such as methanesulphonyl chloride, trifluoromethanesulphonyl chloride or p-toluenesulphonyl chloride, in the presence of alkalis:

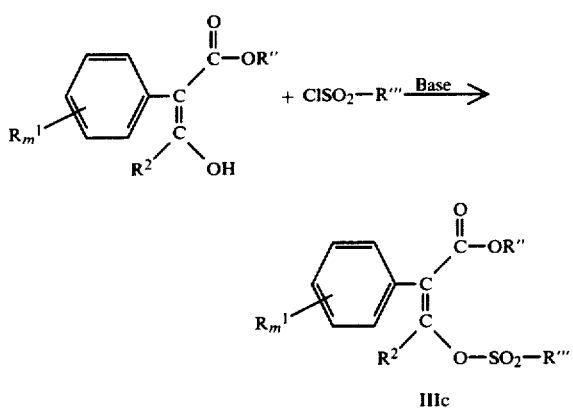

IIIc

Compounds III where R′=Hal are obtained by reacting the hydroxymethylene compounds (III; R′=OH) with inorganic acid chlorides, preferably phosphorus(V) chloride (B. 51, 1366 (1918)).

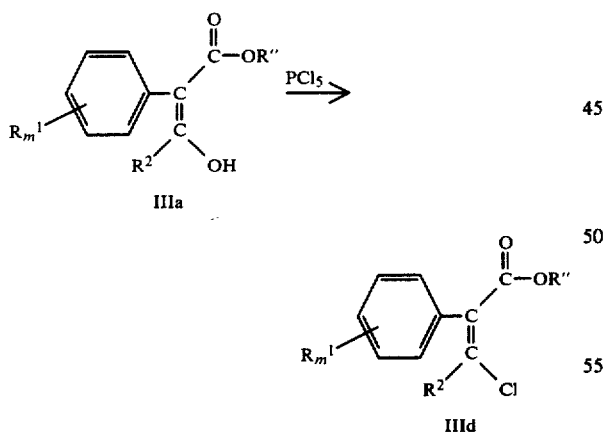

IIId

Compounds III where R′=dialkylamino are obtained by reacting the correspondingly substituted phenylacetic acid alkyl esters with dialkylformamide dialkyl acetals (Tetrahedron Lett. 16, 1361 (1979)), for example

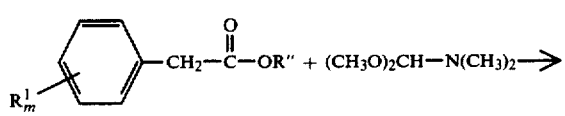

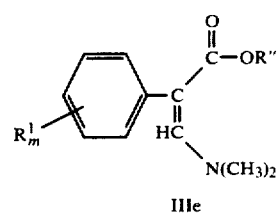

IIIe

Another method for the preparation of these compounds (IIIe) comprises reacting the hydroxymethylene derivatives (IIIa) with secondary amines (A. ch (10) 18, 103, 114 (1932)).

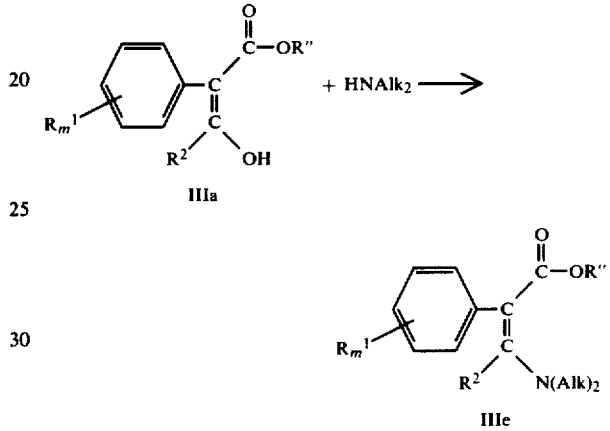

IIIe

To prepare the compounds of the formula III in which R$^2$ represents a lower alkyl radical, in principle the same methods can be used as for the preparation of the compounds where R$^2$=H, but these frequently proceed with inadequate yields. Synthesis of these compounds proceeds with a higher yield if, in accordance with the literature data, the acylation is carried out not with the phenylacetic acid esters but with phenylacetonitriles and the nitrile group is subsequently converted into the ester group:

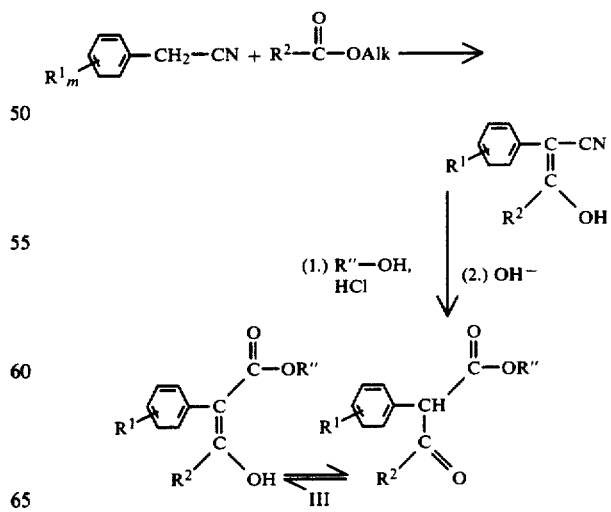

The precursors of the formula IV required for the preparation of the compounds of the formula I according to the invention are known in principle. They are hydrazinopyridines, hydrazino-pyrimidines and hydrazino-1,3,5-triazines:

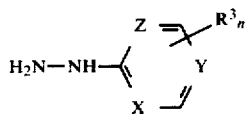
    IV

In formula IV, X, Y and Z denote an N atom or a ring member —CH= or

at least one of the radicals X, Y and Z denoting an N atom, $R^3$ denotes a hydrogen atom, halogen, in particular a chlorine, bromine or fluorine atom, a lower alkyl group with 1 to 4 carbon atoms, which can also be substituted, for example by halogen, in particular fluorine or chlorine, or by a lower alkoxy or alkylmercapto group with 1 to 4 carbon atoms, a nitro group, a cyano group or a carboxylic acid group. The substituent $R^3$, together with one of the adjacent radicals X, Y or Z, where this is a carbon ring member, can also form a fused-on ring, for example a phenylene ring.

n denotes an integer from 0 to 4, but at most a number which corresponds to the number of carbon atoms in the heterocyclic ring.

The preparation of the compounds IV is known in principle. Variants of IV which have not previously been described can be prepared by analogous routes, in particular (a) by reaction of halogeno-N-heterocyclic compounds or alkoxy- or alkylmercapto-N-heterocyclic compounds with hydrazine:

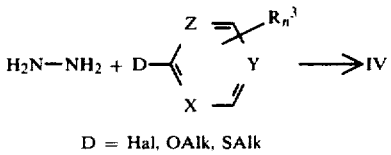

D = Hal, OAlk, SAlk (b) by reduction of heterocyclic diazonium compounds:

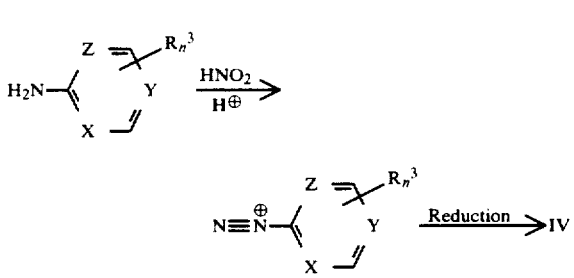

or (c) by reduction of heterocyclic nitramino compounds:

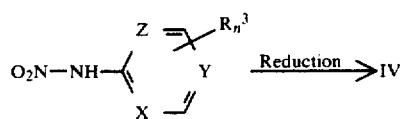

Examples which may be mentioned of intermediates of the formula IV are:

|  | Melting point (°C.)/ boiling point | Literature |
|---|---|---|
| 2-Hydrazino-pyridine | boiling point$_{12}$: 130 | J. Chem. Soc. 107, 691 (1915) |
| 5-Chloro-2-hydrazino-pyridine | 127–128 | |
| 6-Chloro-2-hydrazino-pyridine | 116–117 | |
| 3,5-Dichloro-2-hydrazino-pyridine | 172–174 | |
| 5-Bromo-2-hydrazino-pyridine | 133–134 | |
| 3-Nitro-2-hydrazino-pyridine | 200 | B. 57, 1192 (1924) |
| 5-Nitro-2-hydrazino-pyridine | 204 (decomposition) | E.P. 2471488 |
| 5-Cyano-2-hydrazino-pyridine | 185–186 | |
| 2-Hydrazino-4-methyl-pyridine | 74–75 | Ann. 656, 103 (1962) |
| 2-Hydrazino-6-methyl-pyridine | HCl salt: 194 (decomposition) | |
| 4-Chloro-2-hydrazino-6-methyl-pyridine | 162–163 | |
| 3-Nitro-2-hydrazino-6-methyl-pyridine | 138–139 | J. Am. Chem. Soc. 74, 3828 (1952) |
| 5-Nitro-2-hydrazino-6-methyl-pyridine | 119–121 | |
| 2-Hydrazino-4,6-dimethyl-pyridine | | |
| 3-Cyano-2-hydrazino-6-methyl-pyridine | 243 (decomposition) | |
| 2-Hydrazino-5-trifluoromethyl-pyridine | 68–69 | |
| 4-Hydrazino-pyridine | boiling point$_{187}$: | B. 59, 317 (1926) |
| 4-Hydrazino-2,6-dimethyl-pyridine | | B. 31, 2497 (1898) |
| 3-Chloro-4-hydrazino-pyridine | | |
| 2-Hydrazino-quinoline | 142–143 | J. Chem. Soc. 103 1978 (1913) |
| 2-Hydrazino-4-methyl-quinoline | 145–146 | |
| 4-Hydrazino-quinoline | | |
| 1-Hydrazino-isoquinoline | 172 | Ann. 656, 103 (1962) |
| 2-Hydrazino-pyrimidine | 110–111 | |
| 5-Fluoro-2-hydrazino-pyrimidine | 140–141 | |
| 5-Chloro-2-hydrazino-pyrimidine | 183–184 | |

| | Melting point (°C.)/ boiling point | Literature |
|---|---|---|
| 4-Methoxy-2-hydrazino-pyrimidine | | |
| 2-Hydrazino-4-methyl-pyrimidine | 85–86 | |
| 2-Hydrazino-4,6-dimethyl-pyrimidine | 165 | J. Chem. Soc. 1952, 4691 |
| 4-Methoxy-2-hydrazino-6-methyl-pyrimidine | | |
| 4-Hydrazino-pyrimidine | | |
| 4-Hydrazino-5-methyl-pyrimidine | 205–206 | Bl. Soc. chim. Belg. 68, 30, 32 (1959) |
| 4-Hydrazino-6-methyl-pyrimidine | 140–141 | B. 34, 1241 (1901) |
| 4-Hydrazino-2,6-dimethyl-pyrimidine | 192–193 | Bl. Soc. chim. Belg. 68, 30, 32 (1959) |
| 6-Chloro-4-hydrazino-2-methyl-pyrimidine | 152 (decomposition) | |
| 2-Methoxy-4-hydrazino-6-methyl-pyrimidine | | |
| 5-Methoxy-4-hydrazino-2-methyl-pyrimidine | | |
| 5-Methoxy-4-hydrazino-2 tert. butyl-pyrimidine | 213–214 | |
| 2-Methylmercapto-4-hydrazino-pyrimidine | 143–144 | |
| 2-Methylmercapto-4-hydrazino-6-methyl pyrimidine | 142–143 | |
| 2-Hydrazino-4,6-dimethyl-1,3,5-triazine | | |
| 4-Methoxy-2-hydrazino-6-methyl-1,3,5-triazine | | |
| 4-Methylmercapto-2-hydrazion-6-methyl-1,3,5-triazine | | |
| 4,6-Dimethoxy-2-hydrazino-1,3,5-triazine | 121 | |

The reaction of the substituted atropic acid esters of the formula III with the hydrazino-N-heterocyclic compounds of the formula IV to give the 1-heteroaryl-4-arylpyrazolin-5-ones of the formula I according to the invention takes place in two stages, the terminal NH$_2$ group of the heterocyclic hydrazine first reacting with the enol, enamine or halogenovinyl group in III to give the enehydrazines or hydrazones Ia, and cyclization to give I subsequently taking place, the alcohol or phenol bonded in III being split off.

vantageously, however, both stages are carried out simultaneously or successively in the same mixture.

The reaction of the precursors III and IV with one another to give the compounds of the formula I according to the invention can be carried out without a solvent, by heating the components to temperatures between 50° and 150° C.

The reactions are advantageously carried out in diluents, it being possible to use all the solvents which are inert towards the reaction partners. These include hy-

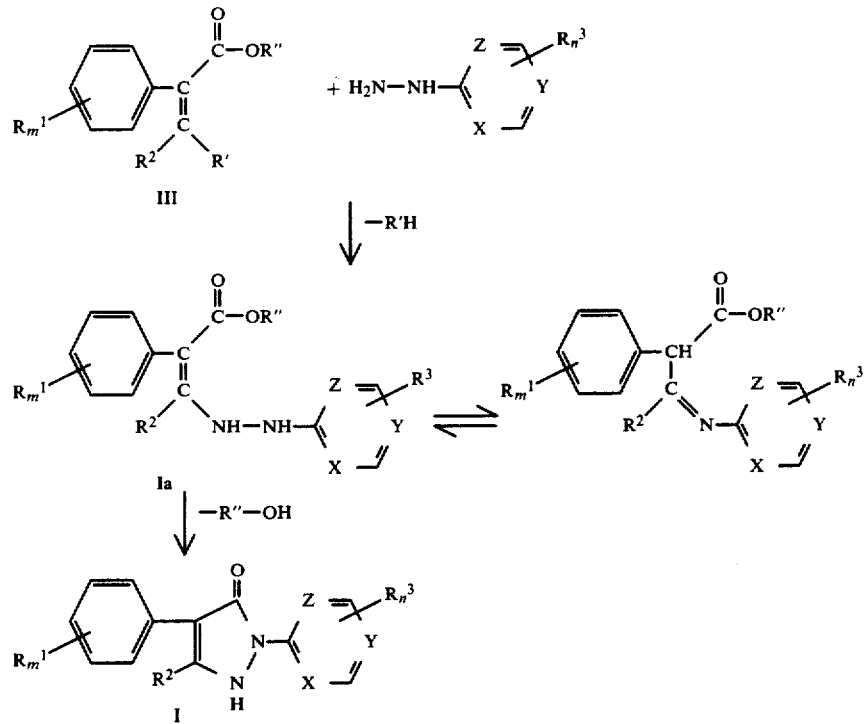

The intermediate stages Ia can be isolated and employed in a pure form in the subsequent reaction. Addrocarbons, such as benzine or toluene, halogenohydrocarbons, such as methylene chloride, chloroform and carbon tetrachloride, alcohols, such as methanol, ethanol, isopropanol and the like, ethers, such as diethyl ether, tetrahydrofuran or dioxane, dimethyl sulphoxide, tetrahydrothiophene dioxide or dimethylformamide. The reactions can also be carried out in water or in mixtures of the solvents mentioned with water.

The reaction temperatures can be varied within a substantial range. In general, the reaction is carried out between about 0° and 100° C., preferably between room temperature and the boiling point of the solvent used.

In many cases, the compounds I are formed from III and IV under the conditions mentioned without further additives. Depending on the leaving group R' in III, however, it is frequently advisable to add bases or acids. The addition of bases is appropriate if R' represents a leaving group which gives an acid, for example a halogen atom as in IIId or an R'''—SO$_2$—O— group as in IIIc. In these cases, the equimolar amount of a base is preferably used. Suitable bases are alkali metal and alkaline earth metal hydroxides and carbonates, alcoholates or tertiary amines, such as triethylamine, pyridine and the like.

The addition of acids is appropriate if the leaving group R' represents a leaving group which gives a base, for example a dialkylamino group as in IIIe. In these cases, the equimolar amount of an acid, for example mineral acids, such as hydrogen chloride or sulphuric acid, or an organic acid, such as acetic acid, is preferably used. A procedure can also be followed here in which the enamines IIIb are converted into a salt, for example by treatment with the equimolar amount of dry hydrogen chloride in inert solvents, and this salt is used.

It may also be advantageous, however, to carry out the reaction in an acid medium when compounds of the formula III where R'=OH (IIIa) or R'=OAlk are used, as a rule amounts below the molar amount of 0.1 to 0.2 mole being sufficient. Instead of subsequent addition of acid, however, a procedure may also be followed in which the hydrazinoheterocyclic compounds of the formula IV are introduced into the reaction not as free bases but in the form of their salts, for example the hydrochlorides. This procedure is particularly advisable if the hydrazines, such as 2-hydrazino-pyridine and 4-hydrazino-pyridine, tend to decompose as free bases.

If an acid medium is used, the reaction as a rule stops at the non-cyclized stage Ia. A neutral or advantageously basic medium is necessary for cyclization to give the compounds I according to the invention. If the first stage of the reaction is carried out in an acid medium, addition of a base is therefore necessary. Preferred possible bases are: alkali metal and alkaline earth metal hydroxides and carbonates, alkali metal and alkaline earth metal alcoholates and alkali metal amides (preferably if the reaction is carried out in an anhydrous medium).

The base is used in at least the amount equivalent to the amount of acid. An excess of up to one more mole may be advantageous, but the medium should correspond to a pH of at least 9. The cyclization stage (Ia→I) is carried out at a temperature between 0° and the boiling point of the solvent used, preferably between 5° and 100°.

Oxidizable intermediate stages occur in an alkaline medium, these manifesting themselves by a yellow to violet coloration. It is therefore advisable to carry out the cyclization reaction in the basic medium in an inert gas atmosphere, for example under nitrogen.

The compounds of the formula I according to the invention form salt-like compounds with bases. Working up of the reaction batches is therefore as a rule carried out by a procedure in which the amount of an acid, for example hydrochloric acid, sulphuric acid or acetic acid, at least equivalent to the base employed is added before the reaction products are isolated. A procedure can also be followed in which the alkali metal or alkaline earth metal salts which as a rule precipitate out of the reaction medium are removed from the reaction mixture by filtration or suction filtration and subsequently treated with at least the equivalent amount of an aqueous acid.

The active compounds can be converted in a known manner into the customary formulations, such as tablets, capsules, dragees, pills, granules, aerosols, syrups, emulsions, suspensions and solutions using inert, non-toxic pharmaceutically suitable excipients or solvents. The therapeutically active compound should in each case be present here in a concentration of about 0.5 to 90% by weight of the total mixture, that is to say in amounts which suffice to achieve the required dosage range.

The formulations are prepared, for example, by extending the active compounds with solvents and/or excipients, if appropriate using emulsifiers and/or dispersing agents, and, for example when using water as the diluent, organic solvents can be used, if appropriate, as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol) and N-alkylpyrrolidones, solid excipients, such as, for example, natural rock powders (for example kaolins, aluminas, talc and chalk), synthetic rock powders (for example highly disperse silicic acid and silicates) and sugars (for example raw sugar, lactose and glucose), emulsifiers, such as non-ionic anionic emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

The formulations are administered in the customary manner, preferably orally or parenterally, in particular cutaneously. In the case of oral use, the tablets can, of course, also contain, in addition to the excipients mentioned, additives such as sodium citrate, calcium carbonate and dicalcium phosphate, together with various adjuvants, such as starch, preferably potato starch, gelatine and the like. Lubricants, such as magnesium stearate, sodium lauryl-sulphate and talc, can furthermore be co-used when making tablets. In the case of aqueous suspensions and/or elixirs which are intended for oral use, the active compounds can be mixed with various flavor-improving agents or colored or coloring substances, in addition to the abovementioned auxiliaries.

In the case of parenteral use, solutions of the active compounds may be employed, using suitable liquid excipients.

In general, it has proved advantageous in the case of intravenous administration to administer amounts of about 0.01 to 10 mg/kg, preferably about 0.05 to 5 mg/kg of body weight daily to achieve effective results, and in the case of oral administration the dosage is about 0.05 to 100 mg/kg, preferably 0.1 to 10 mg/kg of body weight per day.

Nevertheless, it can at times be necessary to deviate from the amounts mentioned, and in particular to do so as a function of the body weight and of the nature of the administration method, but also because of the species of organism and its individual behavior towards the medicament or the nature of its formulation and the time or interval over which administration takes place. Thus it can suffice in some cases to manage with less than the abovementioned minimum amount, while in other cases the upper limit mentioned must be exceeded. Where relatively large amounts are administered, it may be advisable to divide these into several individual administrations over the course of the day. The above statements apply in the general sense in the same manner for administration both in human medicine and in veterinary medicine.

The following examples are intended to illustrate the invention in more detail.

EXAMPLE 1

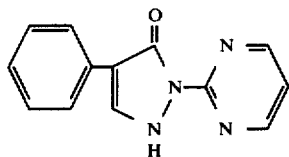

19.2 g (0.1 mole) of ethyl α-hydroxymethylenephenylacetate and 11 g (0.1 mole) of 2-hydrazino-pyrimidine are boiled under reflux in 150 ml of ethanol for 3 hours. The mixture is cooled to room temperature and 9 g (0.1 mole) of concentrated sodium hydroxide solution are then added dropwise, with stirring. The mixture is subsequently stirred at room temperature for 2 hours and is then boiled under reflux for 2 hours. It is neutralized with concentrated hydrochloric acid and diluted with 1 liter of water. The crystals which have separated out are filtered off with suction and dried in air. Yield: 15 g (63% of theory) of 1-pyrimid-2-yl-4-phenyl-pyrazolin-5-one. Melting point: 159° to 160° C. (from ethanol).

EXAMPLE 2

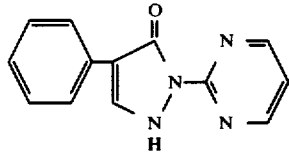

20.6 g (0.1 mole) of ethyl α-methoxymethylenephenylacetate (boiling point$_{0.2}$: 103°-106° C.) are heated under reflux with 11 g (0.1 mole) of 2-hydrazino-pyrimidine in 100 ml of dioxane for 24 hours. The solvent is distilled off in vacuo and the residue is stirred in 50 ml of toluene. 3.2 g (13.5% of theory) of 1-pyrimid-2-yl-4-phenyl-pyrazolin-5-one thereby separate out, and are filtered off with suction and dried. Melting point: 159°-160° C. (from ethanol).

EXAMPLE 3

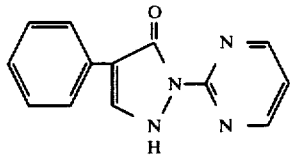

19.2 g (0.1 mole) of ethyl α-hydroxymethylenephenylacetate are dissolved in 100 ml of acetonitrile, 11.2 g (0.1 mole) of potassium tert.-butylate are first added, and 19 g (0.1 mole) of p-toluene-sulphonyl chloride are then added in portions at 20° to 25° C. The mixture is stirred at room temperature for 4 hours and left to stand overnight. The salt which has separated out is filtered off with suction and the filtrate is evaporated in vacuo. The residue is dissolved in toluene and the solution is washed with water, dried over Na$_2$SO$_4$ and evaporated in vacuo. Yield: 23 g (73% of theory) of ethyl α-(4-methyl-phenylsulphonyloxy-methylene)-phenylacetate. The oil is dissolved in 150 ml of ethanol, and 7.7 g (0.07 mole) of 2-hydrazinopyrimidine are then added. The mixture is stirred at room temperature for 10 hours and 13.5 g of concentrated sodium hydroxide solution are then added dropwise in the course of 4 hours. After the mixture has been stirred at room temperature for a further 5 hours, dilute hydrochloric acid is added dropwise to the neutral point and the mixture is diluted with 750 ml of water. The oily product which separates out is taken up in a little water, 3.6 g (22% of theory) of 1-pyrimid-2-yl-4-phenyl-pyrazolin-5-one separating out. Melting point: 159° to 160° C. (from ethanol).

EXAMPLE 4

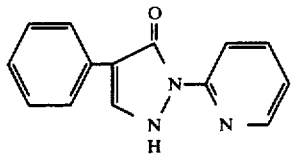

22.7 g (0.1 mole) of the K salt of α-hydroxymethylene-phenylacetic acid ethyl ether and 18.2 g (0.1 mole) of 2-hydrazino-pyridine dihydrochloride are stirred in 200 ml of ethanol at room temperature for 30 minutes and the mixture is then boiled under reflux for 5 hours. After cooling to room temperature, 19.1 g (1.7 moles) of potassium tert.-butylate are introduced, while simultaneously passing nitrogen over. The mixture is stirred at room temperature for 4 hours and left to stand overnight. The precipitate formed is filtered off with suction and suspended in 100 ml of water and the suspension is rendered weakly acid with acetic acid. The crystals are filtered off with suction, washed with water and dried in air. 17.2 g (72.5% of theory) of 1-pyrid-2-yl-4-phenyl-pyrazolin-5-one are obtained. Melting point: 132° to 133° C. (ethanol).

EXAMPLE 5

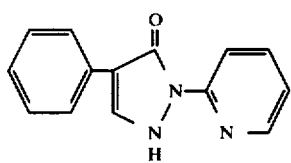

21.2 g (0.1 mole) of phenyl phenylacetate are heated at 100° C. with 11.9 g (0.1 mole) of dimethylformamide dimethyl acetal for 5 hours. All the volatile constituents are then distilled off at this temperature under a waterpump vacuum. The residue, which essentially consists of phenyl α-dimethylamino-methylene-phenylacetate, is dissolved, without further purification, in 100 ml of ethanol, 18.2 g (0.1 mole) of 2-hydrazino-pyridine dihydrochloride are added to the solution and the mixture is boiled under reflux for 5 hours. After cooling, 6.4 g (27% of theory) of the reaction product separate out. This product is filtered off with suction and dried. 18.2 g (0.16 mole) of potassium tert.-butylate are added in portions, at room temperature under nitrogen, to the ethanolic solution which remains. After the mixture has been stirred at room temperature for 5 hours, the precipitate is filtered off with suction and suspended in 100 ml of water and the suspension is acidified with acetic acid. The crystals are filtered off with suction, washed with water and dried in air. A further 8.2 g of the reaction product are thereby obtained. Total yield of 1-pyrid-2-yl-4-phenyl-pyrazolin-5-one: 14.6 g (61.6% of theory).

EXAMPLE 6

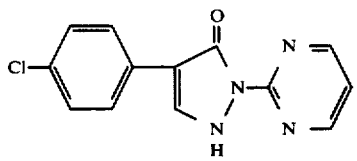

19.9 g (0.1 mole) of ethyl 4-chloro-phenylacetate are heated at 100° C. with 23.8 g (0.2 mole) of dimethylformamide dimethyl acetal for 5 hours. All the volatile constituents are then distilled off at this temperature under a waterpump vacuum. The oily residue, which essentially consists of ethyl α-dimethylaminomethylene-4-chlorophenylacetate, is dissolved, without further purification, in 140 ml of ethanol. 11 g (0.1 mole) of 2-hydrazinopyrimidine and 10 ml of concentrated hydrochloric acid are added. The mixture is heated under reflux for 5 hours, cooled to room temperature and, after addition of 9 g of concentrated sodium hydroxide solution, stirred at room temperature for 5 hours. After neutralization with dilute hydrochloric acid, the mixture is diluted with 1 liter of water. The crystals which have separated out are filtered off with suction, washed with water and dried in air. 7.2 g (26.4% of theory) of 1-pyrimid-2-yl-4-(4-chloro-phenyl)pyrazolin-5-one are obtained. Melting point: 190° to 191° C. (methanol).

The compounds of the following examples were prepared analogously (Table 1).

TABLE 1

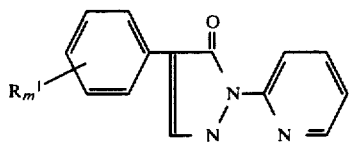

| Example No. | $R^1$ | m | Melting point (°C.) | Recrystallization from |
|---|---|---|---|---|
| 7 | — | 0 | 131–133 | a |
| 8 | 2-F | 1 | 128–130 | g |
| 9 | 4-F | 1 | 137–139 | a |
| 10 | 2-Cl | 1 | 109–111 | a |
| 11 | 3-Cl | 1 | 146–147 | a |
| 12 | 4-Cl | 1 | 175–177 | b |
| 13 | 2-Br | 1 | 108 | b |
| 14 | 2-F, 6-Cl | 2 | 167–168 | b |
| 15 | 2,4-$Cl_2$ | 2 | 168–169 | b |
| 16 | 3,4-$Cl_2$ | 2 | 184–185 | b |
| 17 | 2-$OCH_3$ | 1 | 110–112 | a |
| 18 | 4-$OCH_3$ | 1 | 104–106 | a |
| 19 | 3-$OC_6H_5$ | 1 | 148–149 | b |
| 20 | 3-$OCF_3$ | 1 | 114–116 | a |
| 21 | 4-$OCF_3$ | 1 | 120–122 | g |
| 22 | 4-$SCF_3$ | 1 | 186–188 | a |
| 23 | —O—$CF_2$—O— (3,4-position) | 2 | 179–181 | c |
| 24 | 2-$CH_3$ | 1 | 86–88 | b |
| 25 | 3-$CH_3$ | 1 | 154–156 | a |
| 26 | 4-$CH_3$ | 1 | 132–133 | a |
| 27 | 3-$CF_3$ | 1 | 130–131 | a |
| 28 | 4-$CF_3$ | 1 | 171–173 | b |
| 29 | 2-Cl, 5-$CF_3$ | 2 | 116–118 | g |
| 30 | 3-$CF_3$, 4-Cl | 2 | 204–206 | b |
| 31 | 3,5-$(CF_3)_2$ | 2 | 174–176 | c |
| 32 | —CH=CH—CH=CH— (2,3-position) | 2 | 146 | a |
| 33 | 2-Cl, 5-$CF_3$ | 2 | 116–118 | g |
| 34 | 4-$OC_2H_5$ | 1 | 122 | a |
| 35 | 4-$OC_3H_7$ | 1 | 114–116 | a |
| 36 | 3,5-$(CH_3)_2$ | 2 | 150–152 | a |
| 37 | 4-$COOCH_3$ | 1 | 163–165 | a |
| 38 | 3-$COOC_2H_5$ | 1 | 109–111 | a |
| 39 | 4-NH—CO—$CH_3$ | 1 | 203–205 | f |
| 40 | 4-$SO_2N(CH_3)_2$ | 1 | 212–214 | b |
| 41 | 3-COOH | 1 | 245–247 | a |
| 42 | 4-COOH | 1 | >270 | b |
| 43 | 4-$SO_2$—N=CH—$N(CH_3)_2$ | 1 | 227–229 | f |
| 44 | 4-$SO_2$—N(CH_3)($C_6H_5$) | 1 | 198–200 | b |
| 45 | 3-CO—NH—$C(CH_3)_3$ | 1 | 172–174 | f |
| 46 | 4-$SO_2$—$NH_2$ | 1 | >260 | h + d |
| 47 | 4-CO—NH—$C_6H_5$ | 1 | 242–244 | f |
| 48 | 3,4-O—$CH_2$—O— | 2 | 166–168 | f |

TABLE 2

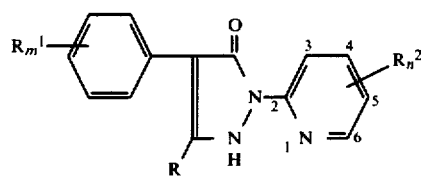

| Example No. | $R^1$ | m | R | $R^2$ | n | Melting point (°C.) | Recrystallization from |
|---|---|---|---|---|---|---|---|
| 49 | — | 0 | $CH_3$ | — | 0 | 114–116 | a |
| 50 | — | 0 | $C_2H_5$ | — | 0 | 72–73 | g |
| 51 | — | 0 | H | 6-Cl | 1 | 155–157 | b |
| 52 | 2-F, 6-Cl | 2 | H | 6-Cl | 1 | 220–221 | f |
| 53 | 3,4-$Cl_2$ | 2 | H | 6-Cl | 1 | 207 | f |
| 54 | 4-$CF_3$ | 1 | H | 6-Cl | 1 | 160–161 | b |
| 55 | — | 0 | H | 5-Cl | 1 | 209–211 | f |
| 56 | 2-Cl | 1 | H | 5-Cl | 1 | 195–197 | b |
| 57 | 3,4-$Cl_2$ | 2 | H | 5-Cl | 1 | 210–211 | b |
| 58 | 2-$OCH_3$ | 1 | H | 5-Cl | 1 | 176–177 | b |
| 59 | 2-$CH_3$ | 1 | H | 5-Cl | 1 | 188–190 | b |
| 60 | 3-$CH_3$ | 1 | H | 5-Cl | 1 | 156–158 | b |
| 61 | 4-$CH_3$ | 1 | H | 5-Cl | 1 | 207 | b |
| 62 | 4-$CF_3$ | 1 | H | 5-Cl | 1 | 218–220 | f |
| 63 | — | 0 | $CH_3$ | 5-Cl | 1 | 156–157 | g |
| 64 | — | 0 | H | 5-Cl | 1 | 164–166 | a |
| 65 | 2-Cl | 1 | H | 3,5-$Cl_2$ | 2 | 198–199 | a |
| 66 | 3,4-$Cl_2$ | 2 | H | 3,5-$Cl_2$ | 2 | 112–114 | f |
| 67 | 2-$CH_3$ | 1 | H | 3,5-$Cl_2$ | 2 | 164–166 | c |
| 68 | 2-$OCH_3$ | 1 | H | 5-Br | 1 | 184–186 | b |
| 69 | — | 0 | H | 5-$NO_2$ | 1 | 264 (decomposition) | f |
| 70 | 4-$CH_3$ | 1 | H | 5-$NO_2$ | 1 | 267–268 | h |
| 71 | 4-$CF_3$ | 1 | H | 5-$NO_2$ | 1 | 196–198 | i and d |
| 72 | — | 0 | H | 6-$CH_3$ | 1 | 110–112 | g |
| 73 | — | 0 | H | 4-$CH_3$ | 1 | 171–173 | b |
| 74 | — | 0 | H | 4,6-$(CH_3)_2$ | 2 | 147–149 | g |
| 75 | — | 0 | H | 4-Cl,6-$CH_3$ | 2 | 214–216 | a |
| 76 | 4-$CF_3$ | 1 | H | 4-Cl,6-$CH_3$ | 2 | 208–210 | a |
| 77 | — | 0 | H | 5-$CF_3$ | 1 | 172–174 | a |
| 78 | — | 0 | H | 5-CN | 1 | 243–245 | b |
| 79 | — | 0 | H | 3-CN,6-$CH_3$ | 2 | 300 | a |
| 80 | 2-Cl | 1 | H | 5-CO—$NH_2$ | 1 | 270 | h |
| 81 | — | 0 | H | —CH=CH—CH=CH—; 4-$CH_3$ (5,6-position) | 3 | 180–182 | b |
| 82 | 3,4-$Cl_2$ | 2 | H | —CH=CH—CH=CH—; 4-$CH_3$ (5,6-position) | 3 | 228–230 | f |
| 83 | 4-$CH_3$ | 1 | H | —CH=CH—CH=CH—; 4-$CH_3$ (5,6-position) | 3 | 196 | b |
| 84 | 4-$CF_3$ | 1 | H | —CH=CH—CH=CH—; 4-$CH_3$ (5,6-position) | 3 | 252–254 | b |

| Example No. | $R_1$ | m | R | $R_2$ | n | F(°C.) | Recrystallization from |
|---|---|---|---|---|---|---|---|
| 85 | — | 0 | $C_3H_7$ | — | 0 | 76–78 | g |
| 86 | — | 0 | H | 6-$CH_3$ | 1 | 110–112 | g |
| 87 | 4-$OCH_3$ | 1 | $CH_3$ | — | 0 | 126–128 | g |
| 88 | 2-F | 1 | $CH_3$ | — | 0 | 98–100 | g |
| 89 | 4-$CH_3$ | 1 | $CH_3$ | — | 0 | 114–115 | g |
| 90 | 4-$OCH_3$ | 1 | $CH_3$ | 5-Cl | 1 | 180–181 | c |
| 91 | 4-$OCH_3$ | 1 | H | 5-Cl | 1 | 167–169 | c |
| 92 | 3,4 $Cl_2$ | 2 | $CH_3$ | — | 0 | 128–130 | g |
| 93 | 4-$OCH_3$ | 1 | H | 4-$CH_3$ | 1 | 146–148 | g |
| 94 | — | 0 | $CH_3$ | 4-$CH_3$ | 1 | 144–145 | g |
| 95 | 3-$CH_3$ | 1 | $CH_3$ | 5-Cl | 1 | 174–176 | g |
| 96 | 4-$CH_3$ | 1 | $CH_3$ | 5-Cl | 1 | 196–198 | g |
| 97 | — | 0 | $CH_3$ | 5-$CH_3$ | 1 | 121–123 | g |
| 98 | — | 0 | H | 5-$CH_3$ | 1 | 170–172 | c |
| 99 | 4-$OCH_3$ | 1 | H | 5-$CH_3$ | 1 | 164–166 | b |

TABLE 3

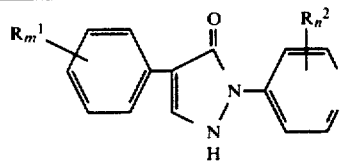

| Example No. | R¹ | m | R² | n | Melting point (°C.) | Recrystallization from |
|---|---|---|---|---|---|---|
| 100 | — | 0 | — | 0 | 242–246 | i |
| 100 | — | 0 | 2,6-$(CH_3)_2$ | 2 | 254 | i |
| 102 | 4-$CF_3$ | 1 | 2,6-$(CH_3)_2$ | 2 | 260–264 | b |

TABLE 5

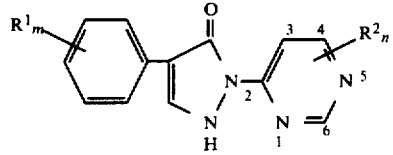

| Example No. | R¹ | m | R² | n | Melting point (°C.) | Recrystallization from |
|---|---|---|---|---|---|---|
| 141 | — | 0 | 4,6-$(CH_3)_2$ | 2 | 192 | b |
| 142 | 4-$CF_3$ | 1 | 4,6-$(CH_3)_2$ | 2 | 196–198 | i |
| 143 | — | 0 | 4-Cl, 6-$CH_3$ | 2 | 162–164 | g |
| 144 | — | 0 | 3-$OCH_3$,6-t-$C_4H_9$ | 2 | 175 | b |
| 145 | 3,4-$Cl_2$ | 2 | 3-$OCH_3$,6-t-$C_4H_9$ | 2 | 196–197 | b |
| 146 | 4-$CF_3$ | 1 | 3-$OCH_3$,6-t-$C_4H_9$ | 2 | 200 | b |
| 147 | — | 0 | 4-$CH_3$,6-$SCH_3$ | 2 | 180–182 | c |
| 148 | 4-$CF_3$ | 1 | 4-$CH_3$,5-$SCH_3$ | 2 | 174–176 | g |

TABLE 4

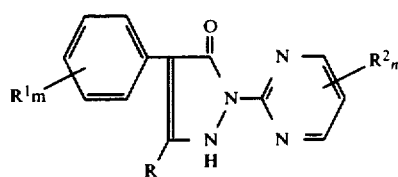

| Example No. | R¹ | m | R | R² | n | Melting point (°C.) | Recrystallization from |
|---|---|---|---|---|---|---|---|
| 103 | — | 0 | H | — | 0 | 158–160 | a |
| 104 | 2-F | 1 | H | — | 0 | 168–170 | a |
| 105 | 4-F | 1 | H | — | 0 | 210–212 | a |
| 106 | 2-Cl | 1 | H | — | 0 | 140–150 | a |
| 107 | 4-Cl | 1 | H | — | 0 | 190–191 | d |
| 108 | 2-Br | 1 | H | — | 0 | 137–138 | a |
| 109 | 2-F, 6-Cl | 2 | H | — | 0 | 178 | b |
| 110 | 2,4-$Cl_2$ | 2 | H | — | 0 | 243–244 | b |
| 111 | 3,4-$Cl_2$ | 2 | H | — | 0 | 246–247 | f |
| 112 | 2-$OCH_3$ | 1 | H | — | 0 | 130 | a |
| 113 | 4-$OCH_3$ | 1 | H | — | 0 | 166–168 | c |
| 114 | 3-$OCF_3$ | 1 | H | — | 0 | 162–164 | c |
| 115 | 4-$OCF_3$ | 1 | H | — | 0 | 170–172 | a |
| 116 | 4-$SCF_3$ | 1 | H | — | 0 | 202–204 | b |
| 117 | —O—$CF_2$—O— (3,4-position) | 2 | H | — | 0 | 230–231 | f |
| 118 | 2-$CH_3$ | 1 | H | — | 0 | 133–134 | b |
| 119 | 3-$CH_3$ | 1 | H | — | 0 | 156–158 | a |
| 120 | 4-$CH_3$ | 1 | H | — | 0 | 168–170 | a |
| 121 | 3-$CF_3$ | 1 | H | — | 0 | 180–181 | b |
| 122 | 4-$CF_3$ | 1 | H | — | 0 | 226 | b |
| 123 | 2-$CF_3$, 4-Cl | 2 | H | — | 0 | 150–152 | a |
| 124 | 2-Cl; 5-$CF_3$ | 2 | H | — | 0 | 182–184 | c |
| 125 | 3-$CF_3$; 4-Cl | 2 | H | — | 0 | 188–189 | a |
| 126 | 3,5-$(CF_3)_2$ | 2 | H | — | 0 | 188–189 | a |
| 127 | —CH=CH—CH=CH— (2,3-position) | 2 | H | — | 0 | 146–148 | b |
| 128 | — | 0 | $CH_3$ | — | 0 | 202–204 | b |
| 129 | — | 0 | H | 5-F | 1 | 245–246 | f |
| 130 | — | 0 | H | 5-Cl | 1 | 267–268 | i |
| 131 | 2-Cl | 1 | H | 5-Cl | 1 | 216–218 | b |
| 132 | 3,4-$Cl_2$ | 2 | H | 5-Cl | 1 | 242–244 | f |
| 133 | 2-$CH_3$ | 1 | H | 5-Cl | 1 | 204 | b |
| 134 | 4-$CH_3$ | 1 | H | 5-Cl | 1 | 264 | b |
| 135 | 4-$CF_3$ | 1 | H | 5-Cl | 1 | 268–270 | f |
| 136 | — | 0 | H | 6-$CH_3$ | 1 | 204–206 | a |
| 137 | — | 0 | H | 4,6-$(CH_3)_2$ | 2 | 256 | c |
| 138 | 4-F | 1 | H | 4,6-$(CH_3)_2$ | 2 | 275 | b |
| 139 | 4-Cl | 1 | H | 4,6-$(CH_3)_2$ | 2 | >270 | h |
| 140 | — | 0 | $CH_3$ | 4,6-$(CH_3)_2$ | 2 | 181–182 | c |

SOLVENTS a. Ethanol
b. Butanol
c. Toluene
d. Methanol
e. Ethyl acetate
f. Dioxane
g. Wash benzine
h. Dimethylformamide
i. Glycol monomethyl ether The biological action of the compounds according to the invention has been demonstrated by the following experiments:

(A) LIPOXYGENASE INHIBITION/CYCLOOXYGENASE INHIBITION/PROSTACYCLIN STIMULATION

1. Lipoxygenase and cyclooxygenase activity in homogenates of RBL-1 cells

Basophilic leukaemia cells from rats (RBL-1) synthesize both lipoxygenase and cyclooxygenase products from $^{14}C$-arachidonic acid with which they are supplied. This results in the possibility of recording the relative potency and selectivity of test substances.

The products formed were separated by thin layer chromatography and quantified in a scanner.

2. Lipoxygenase activity in human PMN leukocytes

The 5-lipoxygenase which is responsible for biosynthesis of the leukotrienes $B_4$, $C_4$ and $D_4$ is selectively inhibited at low concentrations. The polymorphonuclear leukocytes of humans metabolize arachidonic acid to give 5-hydroxy-5,8,11,14-eicosatetraenoic acid (5-HETE) and leukotriene $B_4$ (5S, 12R-dihydroxy-6-cis, 8,10-trans-14ciseicosatetraenoic acid). Inhibition of the release of 5-HETE and leukotriene $B_4$ from leukocytes is a measure of the lipoxygenase-inhibiting effect of the compounds according to the invention.

The test with human leukocytes was carried out by the method of Borgeat and Samuelsson (J. Biol. Chem. 254, 2643, 1979 and Proc. Natl. Acad. Sci. USA, 76, 2148, 1979).

The human PMN leucocytes (>95%) used in the present example were obtained from heparinized whole blood by dextran sedimentation and subsequent density gradient separation (Ficoll-Paque) (compare A. Boyum, Scand. J. Immunol., 5, Suppl. 5, 9, 1976).

$2\times10^7$ cells/ml were suspended in $Ca^{2+}$-containing Dulbecco phosphate buffer and stimulated with the calcium ionophore A 23187 in the presence and absence of lipoxygenase inhibitors. After 15 minutes, the lipoxygenase products were extracted from the acidified incubation medium and separated by means of HPLC.

3. $^3H$-Arachidonic acid metabolism in human platelets (12-lipoxygenase activity and cyclooxygenase activity)

The lipoxygenase-inhibiting and cyclooxygenase-inhibiting properties of the compounds according to the invention were demonstrated analogously to the method of Bailey et al., Journal of Biol. Chemistry 255, 5996, 1980 and in accordance with the method of Blackwell and Flower, Prostaglandins 16, 417, 1978. The metabolism of radioactively labelled arachidonic acid on washed human platelets is utilised in this test method. In this in vitro test, the radioactively labelled metabolites are extracted from the reaction mixture and separated by thin layer chromatography. The autoradiogram is evaluated with a thin layer scanner. Under these test conditions, the labelled metabolites are separated from the unreacted arachidonic acid and can then be evaluated quantitatively. The distribution of the radioactivity in the cyclooxygenase products thromboxane $A_2$ (determined as $TXB_2$) and 12-hydroxy-5,8,10-heptadecatrienoic acid (HHT) formed during the metabolization and the lipoxygenase product 12-hydroxy-5,8,11,14-eicosatetraenoic acid (12-HETE) under the influence of the inhibitors is a measure of the inhibition of the enzymes.

4. Prostacyclin stimulation

The compounds to be used according to the invention also specifically stimulate the synthesis of prostacyclin ($PGI_2$). In contrast to the vasoconstrictor and platelet aggregation-inducing thromboxane, $PGI_2$ has a vasodilating and platelet aggregation-inhibiting action.

(a) Stimulation in whole blood.

Formation of $PGI_2$ can be induced in whole blood by collagen. The endoperoxides formed in platelets are probably converted into $PGI_2$ by leuocyte lipoxygenase. The stable end product of $PGI_2$ utilization, that is to say 6-keto-$PF_1\alpha$, is determined radioimmunologically.

(b) Stimulation in microsomes in vitro.

The specific $PGI_2$-stimulating action was demonstrated in vitro in a mixture of microsomes from sheep seminal vesicles (RVSM) and bovine aortas (BAM) (compare F. Cottee et al., Prostaglandins, 14, 413, 1977). $^3H$-arachidonic acid was incubated with a mixture of RSVM and BAM in the presence of the compounds according to the invention at 25° C. for 10 minutes. The reaction was stopped by acidification to pH 3.5. The fatty acid metabolites were extracted with ethyl acetate. The ethyl acetate was evaporated off under $N_2$, the residue was taken up in $CH_3OH/CHCl_3$ (1:1) and the mixture was applied in thin layer chromatography plastic films. Separation was effected with an eluent mixture of ethylene acetate/glacial acetic acid/isooctane/$H_2O$ (110:20:50:10; organic phase) (P. Needleman et al., The Journal of Clinical Investigation 1978, 61, 839–849). The distribution of the radioactivity was measured by means of a radioscanner.

(B) ALLERGY/ASTHMA AND OTHER DISEASES OF THE RESPIRATORY TRACT

1. Release of mediators from human lungs

Lungs underwent passive sensitization with serum in imitation of the pathophysiological situation (type I-hypersensitivity reaction). Addition of an appropriate specific allergen leads to release of mediators of anaphylaxis, such as histamine, SRS-A, thromboxane and prostaglandins.

Since in humans the lung is the most important target organ for allergic reactions, this test is a relevant model for testing antiasthmatic substances.

2. Passive peritoneal anaphylaxis (rats)

The effect of substances on the release of mediators, in particular the release of leukotrienes, is recorded with this in vivo method. Passive sensitization of peritoneal mast cells from rats with anti-ovalbumin guineapig serum leads, after intraperitoneal injection of the antigen, to release of SRS-A (Smith et al., Int. Arch. Allergy appl. Immunol. 62, 195, 1980). Histamine is not released during this, so that the lipoxygenase-inhibiting action of test substances can be investigated selectively.

(C) INFLAMMATORY DISEASES

The antiinflammatory action of the test substances following oral administration was determined with the aid of carrageenan-induced oedema of the rat paw.

The experiments were carried out with male rats, strain: Bor:WLSW (SPF-Cpb); weight 150 to 220 g. One hour before inducing the oedema (0.1 ml of carrageenan suspension/animal, subplantar injection), the substance to be tested was administered to the animals as a suspension in tragacanth with the aid of a stomach tube; as a control, a second group of animals was treated with tragacanth without the substance.

The paw volumes were measured by the method of F. Kemper and G. Ameln Z. exp. Med. 131, 407 (1959), the difference between the paw volume 5 hours after oedema provocation and the normal paw volume giving the oedema volume.

The $ED_{50}$ of oedema inhibition for the compound of Example 4 (7) following oral administration was first determined by way of example. An $ED_{50}$ of 9.1 mg/kg perorally was calculated from the individual values determined. The following pyrazolinones summarized in Table 5 were investigated in continuing investigations:

(D) PROTECTION AGAINST THROMBOEMBOLISM INDUCED BY ARACHIDONIC ACID

Substances which interfere with prostaglandin and thromboxane biosynthesis act in this model. Rabbits are injected with 1.5 mg/kg Na arachidonate in a marginal ear vein. The animals die within minutes, probably because of vasospastic cyclooxygenase and lipoxygenase products and embolizing platelet thrombi. Literature: Silver, M. J. et al., Science 183, 1085, 1974 Seuter, F., Busse, W. D., Agents and Actions, Suppl. 4, 175, 1979.

(E) INHIBITION OF PLATELET AGGREGATION

Platelets and their adhesion—as well as their aggregating ability—are an essential pathogenetic factor in the formation of thromboses, especially in the arterial branch of the vascular system.

Blood from healthy volunteers of both sexes was used for the in vitro experiments. One part of 3.0% strength aqueous sodium citrate solution was admixed as an anticoagulant to 9 parts of blood. Platelet-rich citrated plasma (PRP) is obtained from this blood by means of centrifugation (literature: Jürgens/Beller, Klinische Methoden der Blutgerinnungsanalyse (Clinical Methods of Blood Coagulation Analysis); Thieme Verlag, Stuttgart 1959).

For these investigations, 0.8 ml of PRP and 0.1 ml of the solution of active compound were preincubated in a waterbath at 37° C. Platelet aggregation was then determined by the turbidometric method (literature: Born, B. V. R., J. Physiol. (London), 162, 67, 1962) in an aggregometer at 37° C. (literature: Therapeutische Berichte 47, 80-86, 1975). For this, 0.1 ml of collagen, an aggregation-inducing agent, was added to the preincubated sample.

The change in optical density in the sample of the PRP was recorded over a period of 6 minutes, and the deflection was determined after 6 minutes. The percentage inhibition in comparison with the control is calculated from these values.

RESULTS

A (1) Lipoxygenase and cyclooxygenase activity in homogenates of RBL-1 cells (Table 2)

As Table 6 shows, many compounds are still effective with >50% inhibition at $5 \times 10^{-7}$ g/ml. Moreover, the selective action on the lipoxygenase is clearly recognizable, and there is only little or no influence on the cyclooxygenase at the concentrations stated.

A (2) Lipoxygenase activity in human PMN leucocytes (Table 1)

As Table 1 shows, almost complete inhibition is still reached at $1 \times 10^{-5}$ g/ml. Benoxaprofen, which is widely used therapeutically, has a weaker action ($IC_{50}$-~$1-5 \times 10^{-5}$ g/ml).

A (3) Lipoxygenase and cyclooxygenase activity in platelets (Table 8)

Parallel to the inhibition of the 5-lipoxygenase in leucocytes, the 12-lipoxygenase in platelets is also inhibited. Influencing of the cyclooxygenase in platelets is an indication of an antithrombotic action of the substances.

A (4) Prostacyclin stimulation

The compounds according to the invention stimulate $PGI_2$ synthesis.

B (2) Passive peritoneal anaphylaxis (rats) (Table 9)

As the table shows, the formation of leukotrienes is almost completely inhibited following oral administration of the substances.

(C) Inhibition of inflammation (Table 10)

The inhibition of an inflammatory reaction in the carrageenan oedema is shown in Table 10.

(D) Thromboembolism

Following oral administration, the compounds according to the invention prevent thromboembolism induced by arachidonic acid.

(E) Inhibition of platelet aggregation

The compounds according to the invention inhibit a collagen-induced aggregation of platelets, which indicates a potential antithrombotic action.

TABLE 6

| Action on lipoxygenase (LO) and cyclooxygenase (CO) in homogenates of RBL−1 cells | | | |
|---|---|---|---|
| Example | Concentration of LO ($\mu$g/ml) | Effect (%) | Concentration of CO ($\mu$g/ml) | Effect (%) |
| 7 | 0.5−1 | −66 | 0.5−1 | +28 |
| 16 | 0.5−1 | −76 | 0.5−1 | −19 |
| 58 | 0.5−1 | −66 | 0.5−1 | −17 |
| 24 | 0.5−1 | −34 | 0.5−1 | −2 |
| 8 | 0.5−1 | −73 | 0.5−1 | +3 |
| 28 | 0.5−1 | −58 | 0.5−1 | +5 |
| 103 | 0.5−1 | −42 | 0.5−1 | ±0 |
| 113 | 0.5−1 | −71 | 0.5−1 | −11 |
| 104 | 0.5−1 | −46 | 0.5−1 | +23 |

TABLE 7

Inhibition of LTB4 synthesis in human PMN's

| Example | Inhibition at 10 µg/ml (%) | Effective threshold concentration (µg/ml) |
|---|---|---|
| 16 | 85 | 1-10 |
| 7 | 92 | 1-10 |
| 8 | 71 | 1-10 |
| 63 | 100 | 1-10 |

TABLE 8

Arachidonic acid metabolism in human platelets

| | Inhibition (threshold concentration in µg/ml) | |
|---|---|---|
| Substance | 12−lipoxygenase | cyclooxygenase |
| 16 | 1-10 | 1-10 |
| 7 | <0.1 | <0.1 |
| 8 | 1-10 | 1-10 |
| 63 | 1-10 | 1-10 |

TABLE 9

Passive peritoneal anaphylaxis (rats)

| Example: | % inhibition following administration of 100 mg/kg perorally |
|---|---|
| 7 | 65 |
| 25 | 64 |
| 27 | 47 |

TABLE 10

Antiinflammatory action of various pyrazolinones
Mode of administration: oral
Dose: 2.5 mg/kg

| Example | % inhibition of the carrageenan oedema |
|---|---|
| 28 | 21% |
| 7 | 44% |
| 130 | 38% |
| 49 | 16% |
| 18 | 22% |
| 135 | 46% |
| 69 | 34% |

It will be understood that the specification and examples are illustrative but not limitative of the present invention and that other embodiments within the spirit and scope of the invention will suggest themselves to those skilled in the art.

We claim:

1. A method of inhibiting lipoxygenase in a patient in need thereof which comprises administering to such patient a lipoxygenase-inhibiting effective amount of a 1-heteroaryl-4-aryl-pyrazolin-5-one of the formula

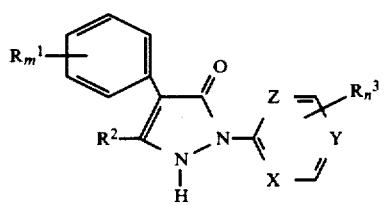

in which $R^1$ is hydrogen, halogen, hydroxyl, optionally substituted lower alkoxy, optionally substituted phenoxy, optionally substituted lower alkylmercapto, optionally substituted lower alkylsulphonyl, optionally fluorine-substituted lower alkyl, a fused-on carbocyclic or heterocyclic radical, carboxyl, lower alkoxycarbonyl or one of the groups

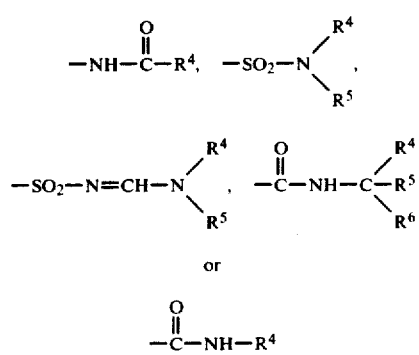

or

wherein $R^4$, $R^5$ and $R^6$ are identical or different and denote hydrogen, lower alkyl or phenyl, m denotes an integer from 1 to 5, $R^2$ denotes hydrogen or lower alkyl X, Y, Z denotes an N atom or a ring member $$\underset{=C-}{\overset{R^3}{|}},$$

at least one of the radicals X, Y or Z denoting an N atom, $R^3$ denotes hydrogen, halogen, lower alkoxy, lower alkylmercapto, lower alkyl, lower halogenoalkyl, nitro, cyano, carboxylic acid amide or a fused-on phenylene radical and n denotes an integer from 1 to 4.

2. The method according to claim 1, in which $R^1$ denotes hydrogen, fluorine, chlorine, methyl, ethyl, methoxy, ethoxy, trifluoromethyl, trifluoromethoxy or trifluoromethylmercapto, m represents the number 1 or 2, $R^2$ denotes hydrogen, methyl or ethyl, $R^3$ denotes hydrogen, fluorine, chlorine methyl, ethyl, methoxy or ethoxy and n represents the number 1 or 2.

3. A method of treating an animal or human patient afflicted with an allergy, asthma, emphysema, shock lung, pulmonary hypertension, inflammation, rheumatism, arthrosis, oedema, thrombosis, a thromboembolism, an ischaemic disorder in peripheral, cardiac or cerebral circulation, a cardiac or cerebral infraction, a disorder in cardiac rhythm, angina pectoris, arteriosclerosis or dermatosis, undergoing a tissue transplant or in need of cytoprotection in the gastrointestinal tract which comprises administering to such animal or human patient a lipoxygenase-inhibiting effective amount of a 1-heteroaryl-4-aryl-pyrazolin-5-one of the formula

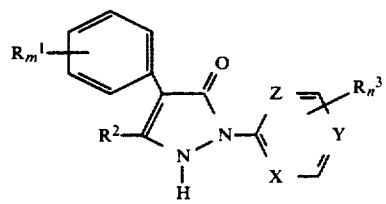

in which $R^1$ is hydrogen, halogen, hydroxyl, optionally substituted lower alkoxy, optionally substituted phenoxy, optionally substituted lower alkylmercapto, optionally substituted lower alkylsulphonyl, optionally fluorine-substituted lower alkyl, a fused-on carbocyclic or heterocyclic radical, carboxyl, lower alkoxycarbonyl or one of the groups

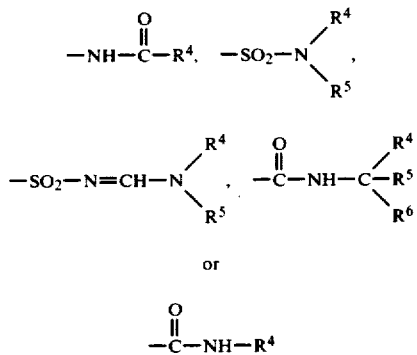

wherein
$R^4$, $R^5$ and $R^6$ are identical or different and denote hydrogen, lower alkyl or phenyl,
m denotes an integer from 1 to 5, $R^2$ denotes hydrogen or lower alkyl,
X, Y, Z denotes an N atom or a ring member

at least one of the radicals X, Y or Z denoting an N atom,
$R^3$ denotes hydrogen, halogen, lower alkoxy, lower alkylmercapto, lower alkyl, lower halogenoalkyl, nitro, cyano, carboxylic acid amide or a fused-on phenylene radical and
n denotes an integer from 1 to 4.
4. The method according to claim 3, in which
$R^1$ denotes hydrogen, fluorine, chlorine, methyl, ethyl, methoxy, ethoxy, trifluoromethyl, trifluoromethoxy or trifluoromethylmercapto,
m represents the number 1 or 2,
$R^2$ denotes hydrogen, methyl or ethyl,
$R^3$ denotes hydrogen, fluorine, chlorine methyl, ethyl, methoxy or ethoxy and
n represents the number 1 or 2.

* * * * *

UNITED STATES PATENT AND TRADEMARK OFFICE
CERTIFICATE OF CORRECTION

PATENT NO. : 4,698,344
DATED : October 6, 1987
INVENTOR(S) : Klaus Sasse, et al.

It is certified that error appears in the above-identified patent and that said Letters Patent is hereby corrected as shown below:

Col. 4, line 36              Beginning of formula delete "Cl"

Col. 13, line 18 in          Correct spelling of --hydrazino--
first column
Col. 14, line 54             End of formula after " ⇌ "
                             insert "NH" as follows:

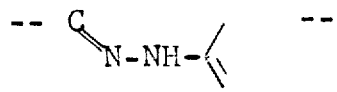

Col. 24, Example No. 148,    Delete "4-$CH_3$,5-$SCH_3$" and substitute
line 8 under "$R^2$"         --4-$CH_3$,6-$SCH_3$--

Col. 26, line 23             Correct spelling of --leucocyte--
Col. 26, line 39             Before "thin" delete "in" and sub-
                             stitute --to--

Signed and Sealed this
Twenty-eighth Day of June, 1988

Attest:

DONALD J. QUIGG

Attesting Officer           Commissioner of Patents and Trademarks